United States Patent
Inouye et al.

(10) Patent No.: US 9,499,825 B2
(45) Date of Patent: Nov. 22, 2016

(54) DUAL INDUCIBLE SYSTEM FOR THE CONDENSED SINGLE PROTEIN PRODUCTION SYSTEM

(75) Inventors: Masayori Inouye, New Brunswick, NJ (US); Lili Mao, Piscataway, NJ (US); S. Thangminlal Vaiphei, Highland Park, NJ (US); Yojiro Ishida, Highland Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 386 days.

(21) Appl. No.: 13/556,100

(22) Filed: Jul. 23, 2012

(65) Prior Publication Data

US 2013/0029426 A1 Jan. 31, 2013

Related U.S. Application Data

(60) Provisional application No. 61/510,766, filed on Jul. 22, 2011.

(51) Int. Cl.
*C12N 15/20* (2006.01)
*C12P 21/02* (2006.01)
*C12N 15/70* (2006.01)

(52) U.S. Cl.
CPC ............... *C12N 15/70* (2013.01); *C12P 21/02* (2013.01)

(58) Field of Classification Search
None
See application file for complete search history.

(56) References Cited

U.S. PATENT DOCUMENTS 7,985,575 B2 7/2011 Inouye et al.
8,183,011 B2 5/2012 Inouye et al.

OTHER PUBLICATIONS

Yamaguchi et al. mRNA Interferases, Sequence-specific endoribonucleases from the toxin-antitoxin systems. Progress in Molecular Biology and Translational Science, vol. 85, pp. 467-500, Feb. 2009.*
Condon, C. Sutdown decay of mRNA. Molecular Microbiology, vol. 61, pp. 573-583, 2006.*
Li et al. Characterization of dual substrate binding sites in the homodimeric structure of *Escherichia coli* mRNA interferaase MazF. Journal of Molecular Biology, vol. 357, pp. 139-150, 2006.*
Vaiphei, ST, Mao, L, Shimazu T, Park, J and Inouye, M. Use of amino acids as inducers for high-level protein expression in the single-protein production system. Applied and Environmental Microbiology, vol. 76, No. 18, pp. 6063-6068, published online Jul. 23, 2010.*

* cited by examiner

*Primary Examiner* — Jennifer Dunston
(74) *Attorney, Agent, or Firm* — Fox Rothschild LLP

(57) ABSTRACT

The present invention provides a dual inducible system for single protein production, as well as a method of inducing high level protein expression using amino acids.

8 Claims, 8 Drawing Sheets

SEQUENCE LISTING

<160> NUMBER OF SEQ ID NOS: 29

<210> SEQ ID NO 1
<211> LENGTH: 36
<212> TYPE: DNA

```
<213> ORGANISM: Artificial Sequence
<220> FEATURE:
<223> OTHER INFORMATION: Synthetic primer for W14F to produce His-less
      MazF

<400> SEQUENCE: 1
gatatgggcg atctgatttt cgttgatttt gacccg                           36

<210> SEQ ID NO 2
<211> LENGTH: 36
<212> TYPE: DNA
<213> ORGANISM: Artificial Sequence
<220> FEATURE:
<223> OTHER INFORMATION: Synthetic Primer for W83L to construct His-less
      MazF

<400> SEQUENCE: 2
gtaaaaagta tcgccctgcg ggcaagagga gcaacg                           36

<210> SEQ ID NO 3
<211> LENGTH: 33
<212> TYPE: DNA
<213> ORGANISM: Artificial Sequence
<220> FEATURE:
<223> OTHER INFORMATION: Synthetic primer for G27K and H28R to construct
      His-less MazF

<400> SEQUENCE: 3
ggtagcgagc aagctaaacg tccagctgtt gtc                              33

<210> SEQ ID NO 4
<211> LENGTH: 20
<212> TYPE: DNA
<213> ORGANISM: Artificial Sequence
<220> FEATURE:
<223> OTHER INFORMATION: Synthetic primer for ompA mRNA

<400> SEQUENCE: 4
gtttttacca taaacgttgg                                             20

<210> SEQ ID NO 5
<211> LENGTH: 14
<212> TYPE: PRT
<213> ORGANISM: Artificial Sequence
<220> FEATURE:
<223> OTHER INFORMATION: Peptide generated from proteins produced by the
      cSPP dual induction

<400> SEQUENCE: 5

Glu Ile Glu Thr Ala Leu Tyr Pro Gly Ser Ile Glu Val Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Peptide generated from proteins produced by the
      cSPP dual induction system

<400> SEQUENCE: 6

His Leu Phe Gln Pro Phe Val Arg
1               5

<210> SEQ ID NO 7
<211> LENGTH: 14
<212> TYPE: PRT
```

```
<213> ORGANISM: Artificial Sequence
<220> FEATURE:
<223> OTHER INFORMATION: Peptides generated from proteins produced by
      the cSPP dual induction system

<400> SEQUENCE: 7

Glu Ile Glu Thr Ala Leu Tyr Pro Gly Ser Ile Glu Val Lys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Peptide generated from proteins produced by the
      cSPP dual induction system

<400> SEQUENCE: 8

His Leu Phe Gln Pro Glu Val Ile Glx
1               5

<210> SEQ ID NO 9
<211> LENGTH: 17
<212> TYPE: PRT
<213> ORGANISM: Artificial Sequence
<220> FEATURE:
<223> OTHER INFORMATION: Peptide generated from protein produced by the
      cSPP dual induction system

<400> SEQUENCE: 9

Ala Trp Phe Gln Val Glu Asp Asp Gln Pro Asp Ile Ala Pro Glu Gln
1               5                   10                  15

Arg

<210> SEQ ID NO 10
<211> LENGTH: 12
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 10

Ala Val Ala Asn Asn Ile Val Val Asn Ala Ala Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Peptide generated from proteins produced by the
      cSPP dual induction system

<400> SEQUENCE: 11

Phe Leu Ile Asn Gly Ser Ser Gln Ala Lys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 12
```

Thr Leu Asp Phe Ser Ile Thr Gly Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 13

Phe Leu Trp Gly Ser Ser Gln Ala Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 14

Thr Leu Asp Phe Ser Thr Pro Gly Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 15

Phe Leu Trp Gly Ser Ser Gln Ala Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 16

Thr Leu Asp Phe Ser Thr Pro Gly Arg
1               5

<210> SEQ ID NO 17
<211> LENGTH: 18
<212> TYPE: PRT
<213> ORGANISM: Artificial Sequence
<220> FEATURE:
<223> OTHER INFORMATION: Peptides generated from proteins produced by
      the cSPP dual induction system

<400> SEQUENCE: 17

Leu Leu Leu Leu Ser Ser Val Arg Pro Ala Ile Ile Pro Thr Glu Glu
1               5                   10                  15

Gln Gln

<210> SEQ ID NO 18
<211> LENGTH: 11
<212> TYPE: PRT

```
<213> ORGANISM: Artificial Sequence
<220> FEATURE:
<223> OTHER INFORMATION: Peptides generated from proteins produced by
      the cSPP dual induction system

<400> SEQUENCE: 18

Ala Ala Ala Ala Val Ala Phe Leu Ser Phe Lys
1               5                   10

<210> SEQ ID NO 19
<211> LENGTH: 18
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 19

Leu Leu Leu Leu Ser Ser Val Arg Pro Ala Thr Ile Phe Thr Glu Glu
1               5                   10                  15

Gln Gln

<210> SEQ ID NO 20
<211> LENGTH: 12
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 20

Ala Ala Ala Ala Val Ala Phe Leu Ser Phe Ile Lys
1               5                   10

<210> SEQ ID NO 21
<211> LENGTH: 18
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 21

Leu Leu Leu Leu Ser Ser Val Arg Phe Ala Ile Ile Pro Thr Glu Glu
1               5                   10                  15

Gln Gln

<210> SEQ ID NO 22
<211> LENGTH: 12
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 22

Ala Ala Ala Ala Val Ala Phe Ile Ser Phe Ile Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: peptides generated from proteins produced by
      the cSPP dual induction system
```

```
<400> SEQUENCE: 23

Leu Thr Asp Glu Glu Val Asp Glu Met Ile Arg
1               5                   10

<210> SEQ ID NO 24
<211> LENGTH: 17
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 24

Glu Ala Phe Ser Leu Phe Asp Lys Asp Gly Asp Gln Thr Ile Thr Thr
1               5                   10                  15

Lys

<210> SEQ ID NO 25
<211> LENGTH: 11
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 25

Leu Thr Asp Glu Glu Val Asp Glu Met Ile Arg
1               5                   10

<210> SEQ ID NO 26
<211> LENGTH: 17
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 26

Glu Ala Phe Ser Leu Phe Asp Lys Asp Gln Asp Gly Thr Ile Thr Thr
1               5                   10                  15

Lys

<210> SEQ ID NO 27
<211> LENGTH: 11
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 27

Leu Thr Asp Glu Glu Val Asp Glu Met Ile Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: peptides generated from proteins produced by
      the cSPP dual induction system

<400> SEQUENCE: 28

Glu Ala Phe Ser Leu Glu Asp Lys Asp Gly Asp Gly Ile Thr Ile Thr
1               5                   10                  15
```

```
Ile Cys

<210> SEQ ID NO 29
<211> LENGTH: 111
<212> TYPE: PRT
<213> ORGANISM: Escherichia coli

<400> SEQUENCE: 29

Met Val Ser Arg Tyr Val Pro Asp Met Gly Asp Leu Ile Trp Val Asp
1               5                  10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
                100                 105                 110
```

DUAL INDUCIBLE SYSTEM FOR THE CONDENSED SINGLE PROTEIN PRODUCTION SYSTEM

PRIORITY CLAIM

This application claims priority to U.S. Provisional Application No. 61/510,766 filed Jul. 22, 2011, the contents of which are hereby incorporated by reference in their entirety.

FIELD OF THE INVENTION

The present invention relates to an efficient and consistent system of single protein production and a method of using same.

BACKGROUND OF THE INVENTION

In *Escherichia coli* (*E. coli*), programmed cell death is mediated through "addiction modules" consisting of two genes, one of which encodes a stable toxic protein (toxin) and the other encodes a short-lived antitoxin. The toxin and the antitoxin are coexpressed from an operon and interact with each other to form a stable complex and their expression is auto-regulated either by the toxin-antitoxin complex or by the antitoxin alone. When their co-expression is inhibited by stress conditions, for example, the antitoxin is degraded by proteases, enabling the toxin to act on its target. Such genetic systems for bacterial programmed cell death have been reported in a number of *E. coli* extrachromosomal elements for the so-called postsegregational killing effect. When bacteria lose the plasmids or other extrachromosomal elements, the cells are selectively killed because unstable antitoxins are degraded faster than their cognate stable toxins. Thus, the cells are addicted to the short-lived antitoxins since their de novo synthesis is essential for cell survival.

The condensed single protein production (cSPP) system was developed based on the endoribonuclease activity of an *Escherichia coli* toxin called MazF, which selectively cleaves cellular mRNAs at the ACA codon sequence. Upon induction of MazF, protein synthesis is completely inhibited, and as a result, cell growth is also completely arrested. However, MazF induced cells are in a quasidormant state, as they are metabolically fully active, producing ATP, amino acids, and nucleotides. Most significantly, in the quasidormant cells, machineries for protein synthesis and mRNA production are also fully functional. Therefore the MazF-induced quasidormant cells are still capable of synthesizing a protein of interest without producing any other cellular proteins, if the mRNA for the protein is engineered to have no ACA sequences. This system is thus termed the single protein production (SPP) system.

One of the most remarkable advantages of the SPP system is that the cell culture can be highly condensed without affecting protein yields. Using this cSPP system, one can achieve a cost savings of as much as 97.5% by condensing a culture 40 fold. This is particularly valuable when highly expensive isotopes or isotope labeled compounds, such as amino acids and glucose, are used for the preparation of protein samples for structural study by nuclear magnetic resonance (NMR) spectroscopy. Furthermore, by use of the cSPP system, amino acid analogues or $D_2O$, which is toxic in conventional protein production systems, reducing protein yields, is not toxic, hardly affecting the final protein yields. However, one drawback of the current cSPP system is the use of IPTG (isopropyl β-D-thiogalactopyranoside) as an inducer for both MazF and a target protein, such that the target protein is also produced at the same time as MazF. Since isotopes or isotopelabeled compounds are added 2 to 3 hours after the addition of IPTG to avoid their incorporation into cellular proteins, nonisotope labeled target protein is also produced during this preincubation period, resulting in a higher background of unlabeled target protein, which may be as high as 20% of the final yield of the target protein produced. The combination of both tetracycline and IPTG inducible systems was employed to separate the inductions of target protein and MazF, respectively. The main disadvantage of this system is that the expression level of target protein critically depends upon tetracycline concentration. The amounts of tetracycline being added to the cells for induction of target protein significantly affect the level of target protein synthesis, especially in the condensed SPP system. Therefore, a highly precise and accurate optimization of the tetracycline level is required for consistency in the expression of target proteins. Thus there remains a need for a more accurate and consistent method of single protein production.

SUMMARY OF THE INVENTION

The present invention is directed to a dual inducible system for the cSPP system, as well as a method of inducing high level protein expression in the single protein production system using amino acids. By taking advantage of MazF, an ACA codon-specific mRNA interferase, *Escherichia coli* cells can be converted into a bioreactor producing only a single protein of interest by using an ACA less mRNA for the protein.

In another embodiment, the present invention provides a method of using the above system for single protein production to suppress production of the unlabeled target protein, as well as increase labeling efficiency and reduce the background attributable to the unlabeled target protein.

In a further embodiment, the present invention is directed to a method of studying functional and/or structural characteristics of a protein using labeled amino acids and/or analogues while eliminating any cytotoxic effects of amino acid analogues on the cells comprising incorporating specific isotope labeled amino acid(s) or toxic (or nontoxic) amino acid analogues.

In yet another embodiment, the present invention provides a method of inducing a target protein comprising: i. transfecting a cell comprising an amino acid auxotroph with a gene encoding a sequence-specific mRNA endoribonuclease and a gene encoding the target protein, wherein the sequence-specific mRNA endoribonuclease has been mutated to remove an amino acid residue corresponding to the amino acid auxotroph; ii. contacting the transfected cell with a composition suitable to induce the sequence-specific mRNA endoribonuclease; and iii. contacting the transfected cell with a composition comprising an amino acid corresponding to the amino acid auxotroph to induce the target protein. In preferred embodiments, the gene encoding a sequence-specific mRNA endoribonuclease is the mazF gene and the composition suitable to induce MazF is IPTG.

In preferred embodiments, the amino acid residue removed from the sequence-specific mRNA endoribonuclease is His or Trp, and the amino acid in the composition used to induce the target protein contains His or Trp, respectively, and the amino acid auxotroph is His auxotroph or Trp auxotroph, respectively.

In preferred embodiments, the steps (i), (ii) and (iii), as described above, are performed sequentially.

In preferred embodiments, the method described above further includes the step of contacting the transfected cells with an isotope-enriched medium for a sufficient time to acclimate the vector to the medium after step (i).

In preferred embodiments, the target protein is not induced by the composition suitable to induce the sequence-specific mRNA endoribonuclease.

In other embodiments, the present invention is directed to a system for expressing a single target protein in a cell comprising: (i) an isolated cell comprising an amino acid auxotroph; and (ii) an expression vector comprising an isolated nucleic acid sequence encoding a sequence-specific mRNA endoribonuclease, wherein the isolated nucleic acid sequence is mutated by removing an amino acid residue corresponding the to amino acid auxotroph.

In preferred embodiments, the system has an expression vector with an isolated nucleic acid sequence encoding a target protein.

In preferred embodiments, the amino acid auxotroph is His auxotroph or Trp auxotroph, and the amino acid residue removed from the isolated nucleic acid sequence is a His residue or a Trp residue, respectively.

In most preferred embodiments, the sequence-specific mRNA endoribonuclease is mazF.

In preferred embodiments, the system includes a composition with an amino acid corresponding to the amino acid auxotroph to induce the target protein.

In other embodiments, the present invention is directed to a method of inducing a toxic target protein comprising: i. transfecting a cell comprising an amino acid auxotroph with a gene encoding a sequence-specific mRNA endoribonuclease, wherein the sequence-specific mRNA endoribonuclease has been mutated to remove an amino acid residue corresponding to the amino acid auxotroph; ii. contacting the transfected cell with a first composition comprising an amino acid residues corresponding to the amino acid auxotroph to produce a sequence-specific mRNA endoribonuclease comprising the amino acid residues of the first composition; iii. contacting the transfected cell of (ii) with a second composition comprising a toxic analogue of the amino acid residues of the first composition to replace the amino acid residues of the first composition in the target protein with the toxic analogues of the second composition; and iv. contacting the transfected cell of (iii) with a composition suitable to induce the target protein with the toxic analogues.

In preferred embodiments, the sequence-specific mRNA endoribonuclease is mazF.

In another preferred embodiment, the present invention is directed to a dual induction system for single protein production comprising modified MazF, with two tryptophan residues in positions 14 and 83 replaced with Phe (W14F) and Leu (W83L), respectively. It further comprises a similar SPP system, constructed using a His-less protein [MazF (ΔH)] and a His auxotroph.

Accordingly, the term "MazF" as used in the specification and claims refers both to the general class of endoribonucleases, and to the particular enzyme bearing the particular name, and is intended to include enzymes having structural and sequence homology thereto. Moreover, it is intended that the invention extends to molecules having structural and functional similarity consistent with their role in the invention. MazF (as well as SPP technology) is described in further detail in U.S. Pat. Nos. 8,183,011; and 7,985,575, the disclosures of which are hereby incorporated by reference in their entireties.

The term "MazE" as used in the specification and claims refers both to the general class of MazE (or MazF modulatory molecules) having structural and/or sequence homology to MazF. Indeed, it is intended that the invention extends to molecules having structural and functional similarity consistent with their role in the invention.

Bacterial cell-death and growth inhibition are triggered by endogenous toxic genes in bacterial genomes in response to certain stress conditions. MazF is an endogenous toxin which causes cell-death and is encoded by an operon called "MazEF addiction module" in *Escherichia coli*. MazE is a labile antitoxin against MazF. As described herein, the effects of MazF on DNA, RNA and protein synthesis were examined in permeabilized cells.

The term "auxotroph" refers to a mutant cell or micro-organism lacking one metabolic pathway present in the parental strain, and that consequently will not multiply on a minimal medium, but requires for growth the addition of a specific compound, such as an amino acid or a vitamin. The term "amino acid auxotroph" refers to a mutant cell or micro-organism lacking one metabolic pathway present in the parental strain, and that consequently will not multiply on a minimal medium, but requires for growth the addition of an amino acid. As used herein, the phrase "amino acid residue corresponding to the amino acid auxotroph" means the specific amino acid residue, lacking in the auxotroph, which is required for growth. For example, the amino acid residue corresponding to a His auxotroph would be a His residue.

The term "endoribonuclease" refers to an enzyme that can cleave RNA internally.

The term "complementary" refers to two DNA strands that exhibit substantial normal base pairing characteristics. Complementary DNA may, however, contain one or more mismatches.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" or "mutated" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO.

Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The present invention also includes active portions, fragments, derivatives and functional or nonfunctional mimetics of MazF polypeptides or proteins of the invention. An "active portion" of a MazF polypeptide means a peptide that is less than the full length MazF polypeptide, but which retains measurable biological activity.

A "fragment" or "portion" of an RNA interferase means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of an mRNA interferase or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original mRNA interferase.

Different "variants" of an mRNA interferase exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to an mRNA interferase, (c) variants in which one or more amino acids include a substituent group, and (d) variants in which an mRNA interferase is fused with another peptide or polypeptide such as a fusion partner, a protein tag or other chemical moiety, that may confer useful properties to an mRNA interferase, such as, for example, an epitope for an antibody, a polyhistidine sequence, a biotin moiety and the like. Other mRNA interferases of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to a person having ordinary skill in the art.

To the extent such allelic variations, analogues, fragments, derivatives, mutants, and modifications, including alternative nucleic acid processing forms and alternative post-translational modification forms result in derivatives of an mRNA interferase that retain any of the biological properties of the mRNA interferase, they are included within the scope of this invention.

The term "homolog" as used herein refers to nucleases encoded by nucleic acid sequences whose polypeptide product has greater than 60% identity to a MazF encoding sequence and/or whose gene products have similar three dimensional structure and/or biochemical activities of MazF. Exemplary homologs include, without limitation, MazF of *Bacillus halodurans* (GENBANK Accession No. NP-244588.1), *Staphylococcus epidermidis* (GENBANK Accession No. AAG23809.1), *Staphylococcus aureus* (GENBANK Accession No. NP-372592.1), *Bacillus subtilis* (GENBANK Accession No. 1NE8_A), *Neisseria meningitides* (GENBANK Accession No. NP-266040.1), *Morganella morgani* (GENBANK Accession No. AAC82516.1) and *Mycobacterium tuberculosis* (GENBANK Accession No. NP-217317.1). The term "homolog" may be used to refer to homologs of a MazF nucleic or amino acid sequence of any species. Such species include, but are not limited to, *E. coli, Bacillus halodurans, Staphylococcus epidermidis, Staphylococcus aureus, Bacillus subtilis, Neisseria meningitides, Morganella morgani, Mycobacterium tuberculosis, Mus musculus,* and *Homo sapiens*. The use of nucleases encoded by such homologs in the methods of the invention is contemplated herein.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID No. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to aimeal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer.

Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

DETAILED DESCRIPTION

Figure 1:
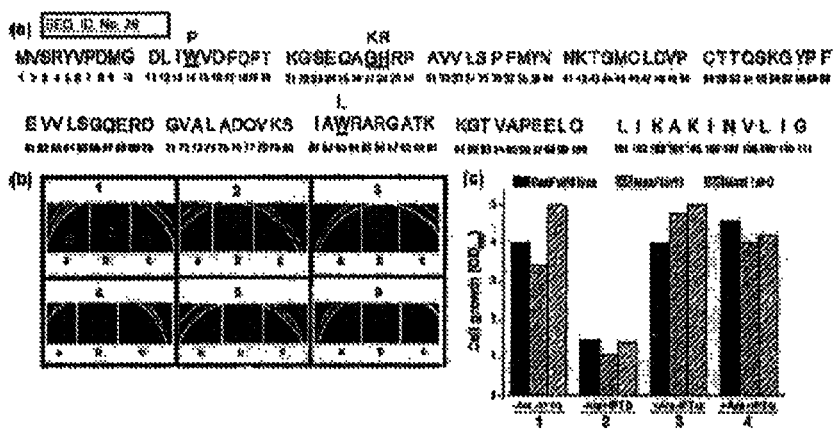
FIGS. 1a-c show the amino acid sequence of MazF and toxicity assay of MazF(ΔW) and MazF(ΔH). (a) Amino acid replacements in MazF(ΔW) and MazF(ΔH). In MazF(ΔW), two tryptophan residues at positions 14 and 83 in MazF were replaced with phenylalanine and leucine, respectively. In MazF(ΔH), the G27 H28 sequence was changed to KR. (b) Plate assay to compare the toxicity of pMazF with those of pMazF(ΔW) and pMazF(ΔH). Panels 1, 2, 3, 4, 5, and 6 correspond to 0.0, 0.05, 0.1, 0.25, 0.5, and 1 mM IPTG, respectively. a, b, and c correspond to pMazF(ΔW), pMazF, and pMazF(ΔH), respectively. (c) Coexpression of MazF and MazE to demonstrate that MazF toxicity was neutralized by MazE production in vivo. For induction of MazF and MazE, 0.1 mM IPTG and 0.2% arabinose, respectively, were added.

The present invention is directed to a dual inducible system for the cSPP system, as well as a method of inducing high level protein expression in the single protein production system using amino acids. It addresses the need currently unfulfilled by existing technologies to induce production of a target protein with a mRNA endoribonuclease, e.g., MazF, with accuracy and consistency. To circumvent the problems associated with using tetracycline especially, the present inventors developed a dual induction system using amino acid auxotrophs. Therefore, preferred embodiments of the present invention are directed to cSPP systems using an amino acid auxotroph to produce a target protein, wherein an amino acid residue corresponding to the amino acid auxotroph is used to induce the target protein. Although both the mazF mRNA and the ACA-less mRNA for the target protein are simultaneously induced in the system of the present invention, only the mazF mRNA is translated in the absence of the amino acid residue corresponding to the auxotrophic E. coli cells, since the residues in MazF are replaced with other amino acid residues while the target protein contains one or more amino acid residues corresponding to the auxotroph. In this manner, only after cellular mRNAs are completely removed can the translation of the ACA-less mRNA for the target protein be initiated by the addition of the amino acid to the medium. For example, E. coli cells from a histidine (His) auxotroph can still produce a protein containing no His residues in the absence of histidine in the medium without producing any other cellular proteins. Therefore, the present inventors have found that even if, e.g., both MazF and a target protein containing, e.g., His residues or tryptophan (Trp) residues, are coinduced by, e.g., IPTG, only His-less MazF or Trp-less MazF would be produced in the absence of, e.g., histidine or tryptophan, by using a His auxotroph or a Trp auxotroph, respectively. In this fashion, the target protein may be induced by the addition of histidine or tryptophan in the medium after His-less or Trp-less MazF induction so that background production of the target protein may be avoided.

In preferred embodiments of the present invention, His and Trp auxotrophs are used, as His and Trp amino acid residues are found in most living cells. However, the present invention contemplates the use of any amino acid auxotroph and its corresponding amino acid residue for protein production. For example, Alanine (Ala), Arginine (Arg), Asparagine (Asp), Cysteine (Cys), Glutamic acid (Glu), Glutamine (Gln), Glycine (Gly), Histadine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val) may all be used as the auxotroph, and corresponding amino acid residues of the present invention. In other preferred embodiments, proteins lacking, e.g., a His residue, can be modified to add a His-tag at the amino terminal end, in which case a His auxotroph can be used for protein production.

With the dual induction systems of the present invention, a target protein can be labeled with isotopes at a very high efficiency, thereby significantly reducing the background due to the unlabeled target protein. The lowering of the background is very important for protein NMR studies, since the unlabeled target protein contributes to a reduced yield of the isotope enriched species and a lower signal to noise ratio in such studies. Thus, in preferred embodiments, the target protein is labeled with isotopes with at least 85% efficiency, at least 90% efficiency, at least 95% efficiency or at least 98% efficiency.

Figure 3:
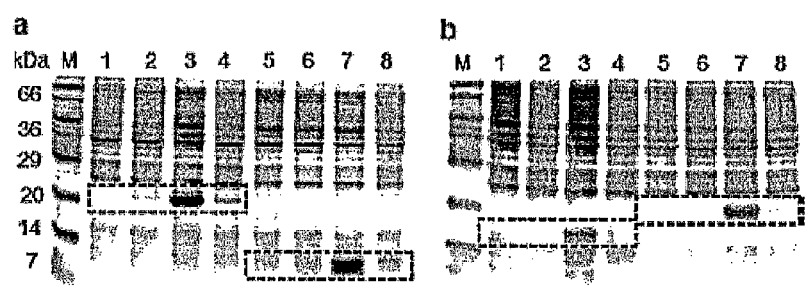
FIGS. 3a-b illustrate the expression profiles of different proteins by using the Trp-inducible SPP system. (a) EnvZB and CspA (lanes 1 to 4 and 5 to 8, respectively); (b) E1B19K150 and GCSF (lanes 1 to 4 and 5 to 8, respectively). Lanes 1 and 5, before IPTG induction; lanes 2 and 6, after 3 h IPTG induction; lanes 3 and 7, overnight incubation in the presence of tryptophan (20 μg/ml); lanes 4 and 8, overnight in the absence of tryptophan; lanes M, molecular weight markers.
Figure 4:
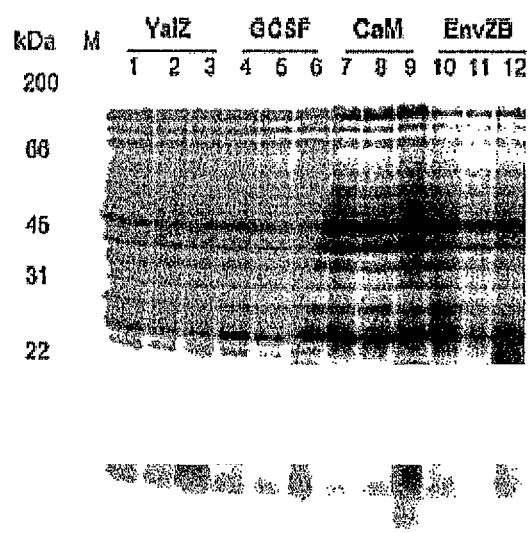
FIG. 4 is a representation of the expression profiles of different target proteins (YaiZ, GCSF, CaM, and EnvZB) by using the His inducible SPP system. Lanes 1, 4, 7, and 10, before IPTG induction; lanes 2, 5, 8, and 11, overnight without histidine; lanes 3, 6, 9, and 12, overnight in the presence of histidine; lane M, molecular weight markers.

In the particular study (see Example 1) described herein, a near absence of unlabeled background protein was achieved at 3 and 24 hours without Trp or His (FIGS. 3 and 4). It is important to note that in the dual induction systems developed, a trace amount of residual Trp or His in the cells could result in translation of target proteins. Therefore, extensive washing of the cells, as well as prior incubation of the cells to deplete residual Trp or His in the cells before induction of the target proteins, was performed. Notably, even proteins which do not contain Trp or His residues can be produced by the present dual induction system simply by adding one Trp residue by use of pColdI(W) or His residues by use of pColdI(SP4) or pColdII(SP4), which add a His tag at the N terminal end of the target protein.

In certain embodiments, the SPP system of the present invention may be used for incorporation of specific isotope labeled amino acid(s). One of the benefits of the SPP system of the present invention is that it allows for complete replacement of all residues of a specific amino acid with an isotope labeled (e.g., $^{13}C$ and $^{15}N$) amino acid. Thus, the development of amino acid auxotrophs to label proteins with only, e.g., Val or Leu is now possible. This provides for new functional and structural study of proteins previously unattainable.

Figure 7:
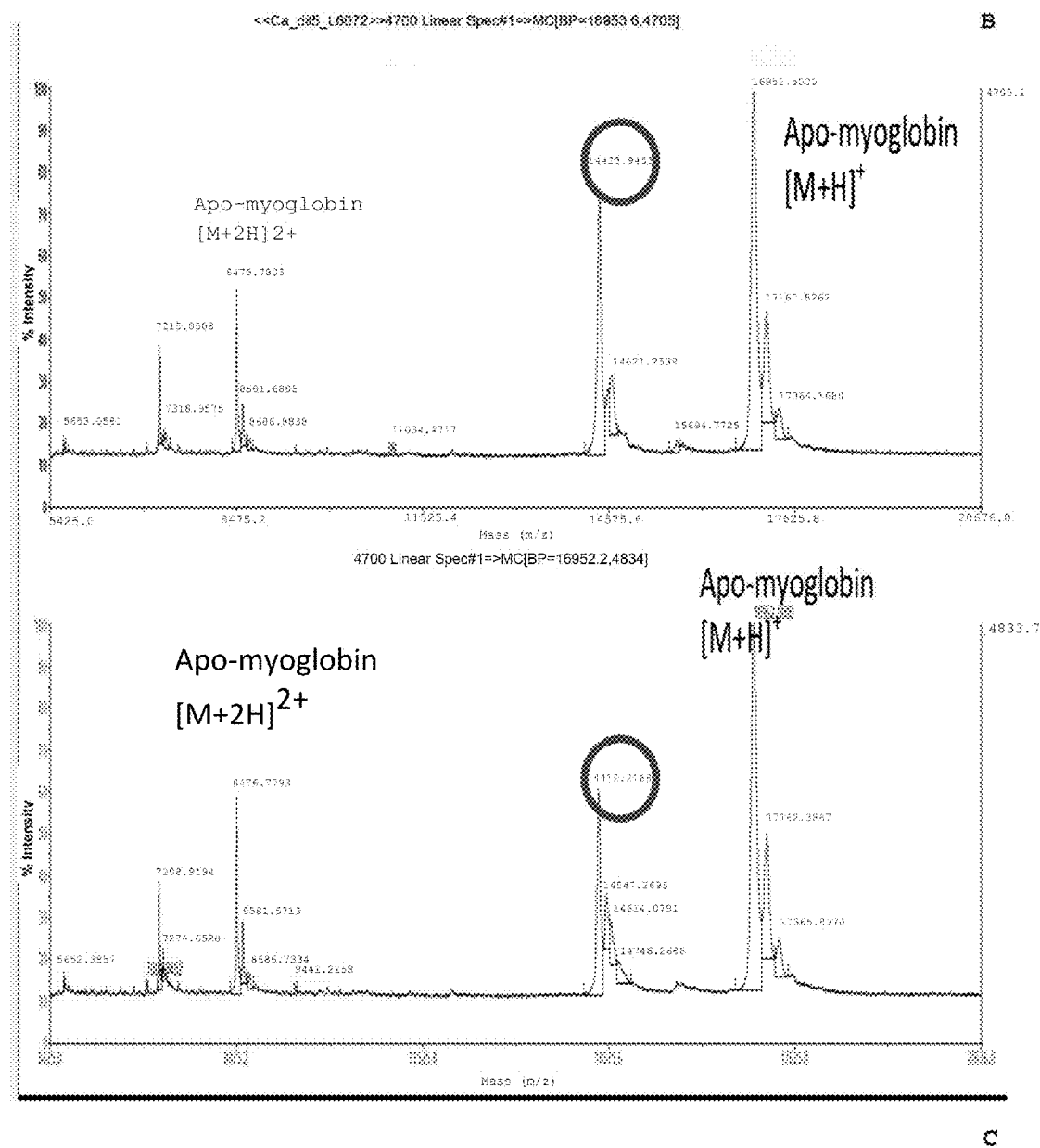
FIGS. 7a-c depict the acquirement of a higher RNA cleavage specificity in MazF-bs(can). (a) shows an analysis of cleavage sites in MS2 phage RNA by MazF-bs(arg) or MazF-bs(can). MS2 RNA was incubated with MazF-bs(arg) or MazF-bs(can) for 1, 5, 10, 30 min. The band in lane M indicates a full length (3.5 kb) of MS2 phage RNA. (b) and (c) show the total mass measurement by MALDI-TOF (Applied Biosystem) of MazF-bs(arg) and MazF-bs(can), respectively. The total mass of MazF(arg) is 14416.661, while the total mass of MazF(can) is 14430.107 as indicated in a circle in the spectra.

In other embodiments, the SPP system of the present invention may be used for complete replacement of all residues of a specific amino acid with its non-natural analogue. For example, the SPP system of the present invention may be used to produce toxic proteins such as canavanine, a non-proteinogenic α-amino acid found in certain leguminous plants, where it accumulated in the seeds of the plant, such as the jack bean. Canavanine's natural amino acid analogue is the proteinogenic α-amino acid L-arginine. Canavanine is highly toxic, and when consumed, canavanine acts to replace the L-arginine in their own cells with Canavanine, which can inhibit proper cell growth and function. Therefore, in previous SPP systems, the attempted induction of canavanine would result in cell death, and growth with not be possible. However, in the present SPP system using an Arg auxotroph, induction of a canavanine protein is possible. See FIG. 7. The SPP system of the present invention can be used for any amino acid analogue/auxotroph combination, e.g., wherein the amino acid auxotroph is a Phe auxotroph and the analogue is a fluoro-compound, such as 4-iodophenylalanine; 4-fluorophenylalanine or 2,4,6-trifluorophenylalanine; wherein the amino acid auxotroph is a Trp auxotroph and the analogue is 7-azatryptophan, 5-hydrotryptophan or 5-fluorotryptophan; wherein the amino acid auxotroph is a His auxotroph and the analogue is 1,2,4-Triazole-3-alanine or 3-methylhistidine; wherein the amino acid auxotroph is an Ile auxotroph and the analogue is 5',5',5'-trifluoroleucine or S-methylcysteine; wherein the amino acid auxotroph is a Leu auxotroph and the analogue is norleucine, trifluoroleucine, Methylthreonine, norvaline, or 4-azaleucine; wherein the amino acid auxotroph is a Tyr auxotroph and the analogue is 3-iodotyrosine, 3,5-diiodo-L-tyrosine or 3-fluorotyrosine; wherein the amino acid auxotroph is a Met auxotroph and the analogue is SelenoMet or ethionine; or wherein the amino acid auxotroph is a Pro auxotroph and the analogue is 3,4-dehydroproline or Azetidyl-2-carboxylic acid.

Figure 8:
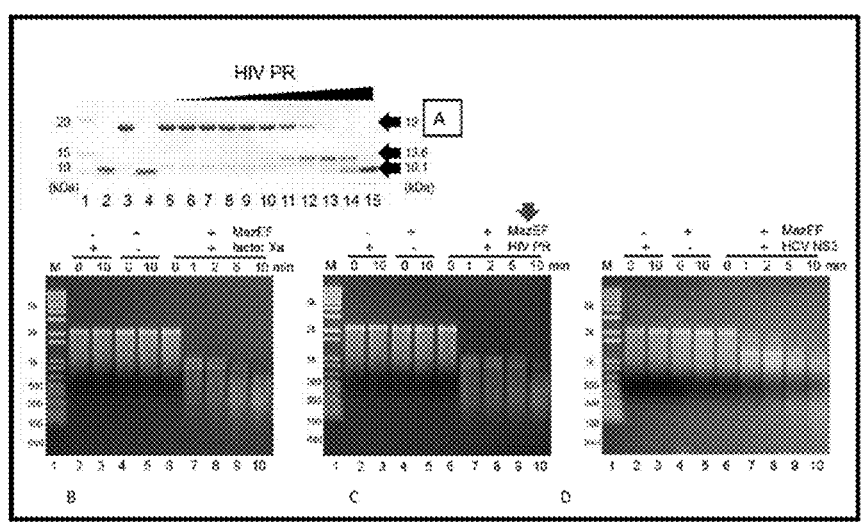
FIGS. 8a-d show the activation of MazF from MazEFpr (factor Xa, HIV1, PR, HCV NS3), showing that the full-size 3.5-kb MS2 phage RNA was digested, only when MazEF-HIV and -HCV were treated with individual proteases. A. Cleavage of MazEF-HIV. Black arrows indicate MazE-MazF fusion protein, MazF, and HIV PR from top to bottom. Lane 1, molecular weight markers; lane 2, HIV PR; lane 3, MazE-MazF fusion protein; lane 4, HIV PR by itself incubated for 30 min; lane 5, MazE-MazF fusion protein by itself incubated for 30 min; lanes 6 to 15, the concentration of HIV PR was increased five times for each lane with a constant amount of the MazE-MazF fusion protein (280 μM). Thus, the molar ratios between HIV PR and MazE-MazF fusion protein changed from 3×10-6:1 (lane 6) to 1.6:1 (lane 15). Activation of MazF from the MazE-MazF fusion protein by factor Xa, HIV PR and HCV NS3 protease is shown in B, C and D, respectively. The MazF activity was measured with MS2 phage RNA as substrate.

Further, the SPP system of the present invention may be used to engineer mRNA interferases. By swapping a domain between two homologues, e.g., MazF homologues, it is possible to create a new mRNA interferase having new RNA cleavage specificities. Even further, it is possible to fuse a mRNA interferase with its antitoxin with a virus specific protease. For example, MazF can be fused with its antitoxin, MazE, with HIV specific protease, HIVpr to create HIV-infection activating MazF. By using the SPP system of the present invention, only HIV infected cells would be killed. See FIG. 8.

This is yet another benefit of the SPP system of the present invention, as it can be used to screen for potential therapeutic compositions. The SPP system of the present invention is supposed to block cell growth completely. However, particular protein expression in the presence of channel inhibitors can be found to override the cell growth inhibition caused by the SPP system. Hence, simple measurement of *E. coli* cell growth occurring only in the presence of effective inhibitors may be used for the high throughput drug screening instead of its tedious biological analysis. See Example 2.

EXAMPLES

The present invention is described more fully by way of the following non limiting examples. Modifications of these examples will be apparent to those skilled in the art.

Example 1

Two amino acid auxotrophs of Trp and His were used to construct a dual induction SPP system. For this purpose, both Trp-less proteins and His-less MazF proteins [MazF (ΔW) and MazF(ΔH), respectively] were generated to create the new SPP system. MazF was engineered by replacing two tryptophan residues in positions 14 and 83 with Phe (W14F) and Leu (W83L), respectively. A similar SPP system was also constructed with the use of a His-less protein [MazF (ΔH)] and a His auxotroph. See FIG. 1. Using these dual induction systems, isotopic enrichments of $^{13}$C, $^{15}$N, and $^{2}$H were highly improved by almost complete suppression of the production of the unlabeled target protein. In both systems, isotopic incorporation reached more than 98% labeling efficiency, significantly reducing the background attributable to the unlabeled target protein.

Figure 5:
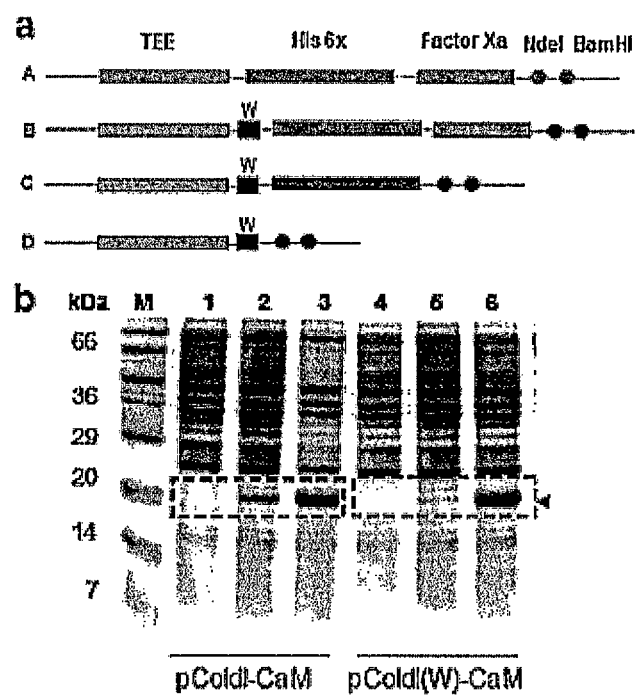
FIGS. 5a-b show the expression of Trp-less protein for the Trp induction system, (a) pCold vectors used in this study were pColdI(SP4) (structure A), pColdI(W) (structure B), pColdII(W) (structure C), and pColdIII(W) (structure D). (b) Expression of a Trp-less human calmodulin by using the dual-induction SPP system. Lanes 1 and 4, before IPTG induction; lanes 2 and 5, after 3 h IPTG induction; lanes 3 and 6, overnight in the presence of tryptophan (20 μg/ml); lane M, molecular weight markers.

A number of proteins, such as (i) E. coli EnvZB, which is the ATP binding domain of the histidine kinase EnvZ (161 residues); (ii) E. coli CspA, which is the major cold shock protein (70 residues); (iii) E. coli YaiZ, which is a plasma membrane protein (80 residues); (iv) the antiapoptotic adenoviral protein EIB19K150 (150 residues); (v) human granulocyte colony stimulating factor (GCSF; 175 residues); and (vi) human calmodulin (CaM), which is a calcium binding protein (148 residues), were tested using the SPP system described above. See FIGS. 3 and 4. It was found that isotope incorporation into these proteins was very tightly regulated so that the background due to the unlabeled target protein was significantly reduced. A pCold(W) system in which a Trp tag can be added to the N terminal part of a protein was also created so that the dual induction expression can still be applied for Trp-less proteins. See FIG. 5.

Construction of MazF Variants

Two MazF variants, MazF(ΔW) and MazF(ΔH), were constructed by site directed mutagenesis. For MazF(ΔW), Trp14 and Trp83 in pMazF were replaced with Phe and Leu, respectively. To construct His-less MazF(ΔH), Gly27-His28 was altered to Lys-Arg. Primers used for MazF(ΔW) and MazF(ΔH) were as follows: for W14F, 5'-GATATGGGC-GATCTGATTTTCGTTGATTTTGACCCG-3'(SEQ ID NO. 1); for W83L, 5'-GTAAAAAGTATCGCCCT-GCGGGCAAGAGGAGCAACG-3'(SEQ ID NO. 2); and for G27K and H28R, 5'-GGTAGCGAG-CAAGCTAAACGTCCAGCTGTTGTC-3'(SEQ ID NO. 3). Both sets of mutations were confirmed by sequencing the DNA of the individual plasmids pMazF(ΔW) and pMazF(ΔH).

Construction of Trp and His Auxotrophs

In order to construct Trp auxotroph BL21(DE3) ΔtrpC and His auxotroph BL21(DE3) ΔhisB, phage lysates were prepared from the JW1254 and JW2004 strains, respectively, from the Keio collection (1) by using the P1 transduction method described in the ad. The ΔtrpC and ΔhisB lysates were used to transfect BL21(DE3) cells, which were then plated on agar plates with or without tryptophan and histidine, respectively. The colonies which appeared on the plates were confirmed for the presence or absence of kanamycin cassettes by colony PCR technique using specific primers. The BL21(DE3) ΔtrpC and BL21(DE3) ΔhisB auxotrophs were also confirmed by their inability to grow in the absence of tryptophan and histidine, respectively. Competent cells derived thereof were transformed with pMazF (ΔW) and pMazF(ΔH), respectively. The obtained plasmid bearing transformants were stored at −80° C., after being frozen in liquid nitrogen, until further use.

Toxicity Test for pMazF(ΔW) and pMazF(ΔH)

To determine the toxicities of the pMazF variants, pMazF, pMazF(ΔW), and pMazF(ΔH) were transformed in BL21 (DE3) cells, which were then plated on LB plates containing chloramphenicol. A single colony from each plate was resuspended in 200 μl of LB broth, and 5 μl volumes of each were dropped on LB plates containing 0, 0.05, 0.1, 0.25, 0.5, and 1 mM IPTG. The plates were dried and incubated for at least 24 h at room temperature or overnight at 37° C.

In order to show whether the toxicity of MazF was neutralized by its antitoxin (MazE), pMazF and the pMazF variants were cotransformed with pBADMazE and overnight cultures were transferred and grown in 20 ml LB broth. When the optical density at 600 nm (OD$_{600}$) reached about 0.4 to 0.5, the three different cultures were equally distributed into four sets of tubes (see FIG. 1c). In the first set, neither IPTG nor arabinose was added; in the second, only IPTG was added. The third set contained only arabinose, and the fourth set contained both IPTG and arabinose. Arabinose was added (0.2%) prior to the addition of IPTG for the production of antitoxin MazE.

Primer Extension Analysis

Primer extension analysis was also carried out to determine the specificity of MazF cleavage sites in vivo. Total RNA was extracted from BL21(DE3) cells containing pMazF, pMazF(ΔW), or pMazF(ΔH) after induction with 1 mM IPTG for 10 min at 37° C. Primer extension was carried out at 47° C. for 1 h with 10 units of avian myeloblastosis virus (AMV) reverse transcriptase (Roche) by using 15 μg of total RNA and 1 μmol of the appropriate primer labeled with [γ-32P]ATP through the use of T4 polynucleotide kinase (Takara Bio). A specific primer for ompΔ mRNA, 5'-GTTTTTACCATAAACGTTGG-3' (SEQ ID NO. 4), was used for all the reactions. The reaction was stopped by the addition of 12 μl of sequencing loading buffer (95% formaldehyde, 20 mM EDTA, 0.05% bromophenol blue, 0.05% xylene cyanol), and the reaction mixture was heated at 95° C. for 2 min and then placed on ice. The products were analyzed using a 6% polyacrylamide gel containing 8 M urea, with a sequencing ladder made with the same primer.

Trp-Inducible SPP System

The plasmid pColdI(SP4) or pColdI(W) bearing ACA less-genes for EnvZB, CspA, E1B19K150, GCSF, and CaM was transformed into BL21(DE3) ΔtrpC competent cells containing pMazF(ΔW). After overnight incubation at 37° C., colonies were inoculated in 50 ml of M9 medium containing tryptophan (20 μg/ml), ampicillin (100 μg/ml), and chloramphenicol (25 μg/ml). The overnight culture from 37° C. was washed with M9 medium and transferred to 1 liter of M9 medium containing tryptophan along with the appropriate antibiotics, The cells were allowed to grow until the OD$_{600}$ reached 0.5 to 0.6 at the same temperature, after which they were washed two or three times with isotope enriched M9 medium and resuspended in Trp-less and isotope enriched M9 medium containing [$^{15}$N]NH$_4$Cl, [$^{13}$C] glucose (deuterated), or $^{2}$H$_2$0. This was followed by a cold shock on ice for 5 min, an acclimatization at 15° C. for 45 min, and a 20 times condensation of the culture as described previously. The cells were incubated for an additional 45 min at this temperature, and IPTG was added at a final concentration of 0.1 to 0.5 mM to induce MazFΔW expression. After 3 h of incubation at 15° C., Trp (20 μg/ml) was added to induce target protein production for the next 16 to 24 h until the cells were harvested.

His Inducible SPP System

In this system, the BL21(DE3) ΔhisB host cell containing pMazF(ΔH) was used for transformation of pColdI(SP4) bearing ACA-less genes for YaiZ, GCSF, CaM, and EnvZB. Colonies from overnight plates were used for inocuhun in 50 ml of M9 medium supplemented with histidine. The cells were washed with M9 medium and finally transferred to 1 liter of M9 medium containing histidine and appropriate antibiotics (ampicillin and chloramphenicol). The cells were allowed to grow at 37° C. until the $OD_{600}$ reached 0.5 to 0.6, after which they were washed three times using isotope enriched M9 medium. The cells were then resuspended in His-less M9 medium, followed by cold shock and acclimatization as described in the previous section. After 3 h of induction with IPTG, the cells were washed again and finally resuspended in isotope enriched M9 medium containing histidine (20 μg/ml) to induce target protein production for the next 16 to 24 h until the cells were harvested.

Mass spectrometric analyses for isotopic incorporation—For mass spectrometric analyses of isotope labeled target proteins, the isotope-labeled target protein bands were excised from SDS PAGE gel, The protein band was treated with trypsin and subjected to liquid chromatography mass spectrometry (LC-MS) for further analysis as described in the art.

Results

Removal of Trp and His Residues from MazF

The wild type MazF contains two Trp residues and one His residue (FIG. 1a). To construct Trp-less MazF, Trp14 and Trp83 were replaced with Phe and Leu, respectively, in pMazF to create pMazF(ΔW). To construct His-less MazF, Gly27 His28 was altered to Lys Arg to create pMazF(ΔH). For both plasmids, the mazF gene is under the control of the IPTG inducible lac promoter so that gene expression can be induced by the addition of IPTG. The toxicities of these mutated MazF proteins were examined on plates containing various concentrations of IPTG by using E. coli BL21(DE3) cells carrying pMazF, pMazF(ΔW), or pMazF(ΔH). As shown in FIG. 1b, both MazF mutants showed toxicity almost identical to that of wild type MazF in all IPTG concentrations tested, indicating that the amino acid substitutions did not affect MazF toxicity. As well, in the demonstration that these MazF variants could inhibit cell growth independently of MazF endoribonuclease activity, coexpression with MazE, an inhibitor of MazF, was also found to revert the toxic effect, as shown in FIG. 1c (panel 4). In the absence of MazE, induction of MazF by IPTG resulted in cell growth inhibition (FIG. 1c, panel 2), Notably, the Trp and His residues are not conserved in MazF homologues, also supporting the notion that these residues do not play crucial roles in the enzymatic activity of MazF.

Specific Enzymatic Activities of MazF Variants

Figure 2:
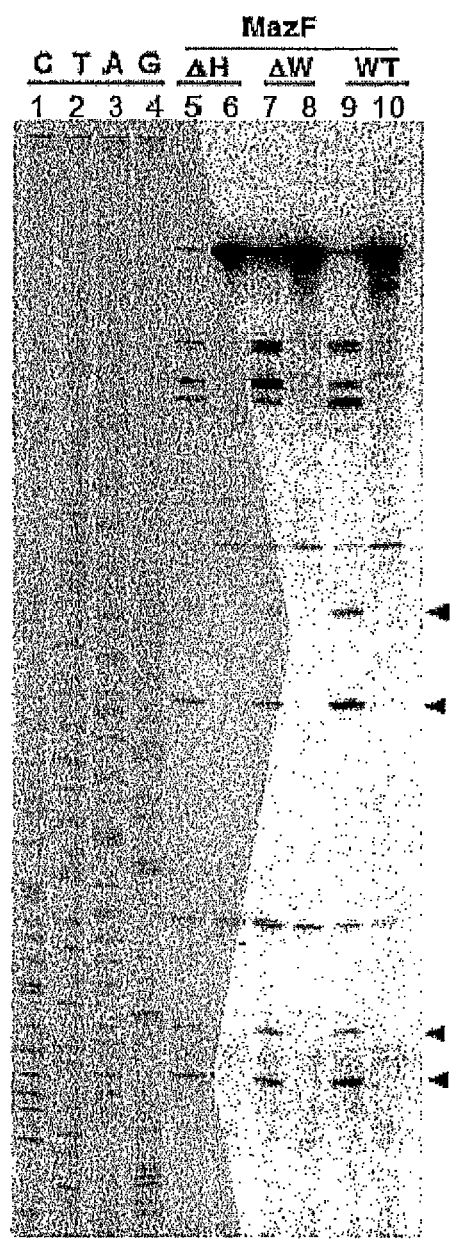
FIG. 2 depicts a primer extension analysis of MazF and MazF variants. Total RNA was extracted from both the induced and uninduced cells bearing pMazF, MazF(ΔW), and MazF(ΔH). Primer extension was carried out using an ompA mRNA specific primer as described in Materials and Methods. This result shows that identical bands were produced from all the RNAs extracted from induced cultures, suggesting their similar MazF cleavage sites (lanes 5, 7, and 9). Lanes 6, 8, and 10 represent the same from the uninduced cultures (wild type [WT]

The toxic effects of the MazF variants alone could not entirely support the fact that the specificity of the cleavage sites still remained the same. To demonstrate that the cleavage sites of MazF variants had not been altered, primer extension analysis was carried out using ompΔ mRNA as the template. The primer extension analysis of ompA using a specific primer showed distinct bands exhibiting the specific cleavage sites after induction of MazF by IPTG (FIG. 2). These bands were identical in MazF(ΔW) and MazF(ΔH), as well as in the wild type MazF, where the cleavage occurred before or after the A residue of ACA sequences (FIG. 2, lanes 5, 7, and 9, respectively). This result clearly indicates that both the MazF variants cleaved mRNAs at the specific sequence ACA in vivo.

Use of pMazF(ΔW) and pMazF(ΔH) in the SPP System

For construction of a Trp auxotroph, the gene for trpC was deleted by replacement with a kanamycin resistance gene, creating BL21(DE3) Δtrp from BL21(DE3). For construction of a His auxotroph, the gene for hisB was deleted by replacement with the same kanamycin resistance gene, creating BL21(DE3) Δhis. First, these deletion strains were transformed with pMazF(ΔW) and pMazF(ΔH) and used as hosts for the SPP expression of several proteins, such as CspA, EnvZB, OmpX, E1 B19K150, YaiZ, CaM, and GCSF. All their genes were engineered to be ACA free without altering the encoded amino acid sequences, and their codon usages were optimized for expression in E. coli.

Note that since all proteins tested contain at least one Trp residue (one Trp residue in CspA, two in GCSF, three in EnvZB, and seven in E1B19K150), their syntheses were also stopped even though their mRNAs lack ACA sequences. After 3 h of incubation, tryptophan was added to the medium to initiate the production of the target protein, and EnvZB was expressed very well after overnight incubation (FIG. 3a, lane 3). With EnvZB, after 3 h of IPTG induction but before the addition of tryptophan, very little EnvZB was produced (FIG. 3a, lane 2). After overnight incubation without the addition of tryptophan, very little production of the protein was detected (FIG. 3a, lane 4), and this was likely due to the generation of Trp by degradation of the endogenous proteins during the incubation. Note that identical amounts of culture were applied in all lanes and no changes in the amounts of all cellular proteins (except for EnvZB) were observed. This indicates that no significant amount of cellular protein was produced during the overnight culture.

CspA, E1B19K150, and GCSF were also expressed in the same manner as EnvZB, as shown in FIG. 3a, lanes 5 to 8, and b, lanes 1 to 4 and lanes 5 to 8, respectively. In all cases, the target proteins were produced in high yields (FIG. 3a, lane 7, and b, lanes 3 and lane 7, respectively) with very low background production before the addition of tryptophan (FIG. 3a, lane 6, and b, lanes 2 and 6, respectively). Also, overnight production of the target proteins without the addition of tryptophan was very low in all cases (FIG. 3a, lane 8, and b, lanes 4 and 8, respectively). These results demonstrate that protein production can be very tightly controlled by tryptophan by using a Trp auxotroph and effectively induced by the addition of tryptophan in the SPP system.

We also carried out the same experiments with a His auxotroph expressing YaiZ, GCSF, CaM, and EnvZB as shown in FIG. 4 (lanes 3, 6, 9, and 12, respectively). In all cases, their expression was tightly regulated by the addition of histidine, with very low background production of these proteins before the addition of histidine. Since pCold vectors already contain one or more His residues, this system can be used for expression of His-less proteins by using the normal pCold vectors.

Controlled Protein Synthesis by a Single Amino Acid for Trp-Less Proteins

In the experiments described above, Trp and His were chosen, as these residues exist in most proteins. However, some proteins may not contain these residues. For this reason, we created a new vector system which adds a Trp residue at the N-terminal end of the protein of interest. To each of the pCold vectors, pColdI(SP4), pColdII(SP4), and pColdIII(SP4), developed for the SPP system, a TGG codon for Trp was added immediately after the translation enhancing element (TEE), as shown in FIG. 5a. These vectors were designated pColdI(W), pColdII(W), and pColdIII(W), respectively. We tested pColdI(W) for the production of human CaM, a protein of 148 residues that does not contain Trp. The gene for CaM was engineered to be ACA free, and its codon usage was optimized for E. coli. It was subsequently cloned into pColdI(W), as was pColdI as a control. It is important to note that neither vector contains ACA sequences in its transcript.

There is a substantial difference in the amounts of target protein produced with pColdI and pColdI(W) after 3 hours of IPTG induction but before Trp addition (FIG. 5b, lanes 2 and 5, respectively). The presence of one Trp residue in pColdI(W) suppressed the production of CaM very efficiently when Trp was not added to the medium containing IPTG (FIG. 5b, compare lanes 5 and 2).

Isotopic Incorporation with $^{15}$N—, $^{13}$C, and $^{2}$H-Enriched Media

Figure 6:
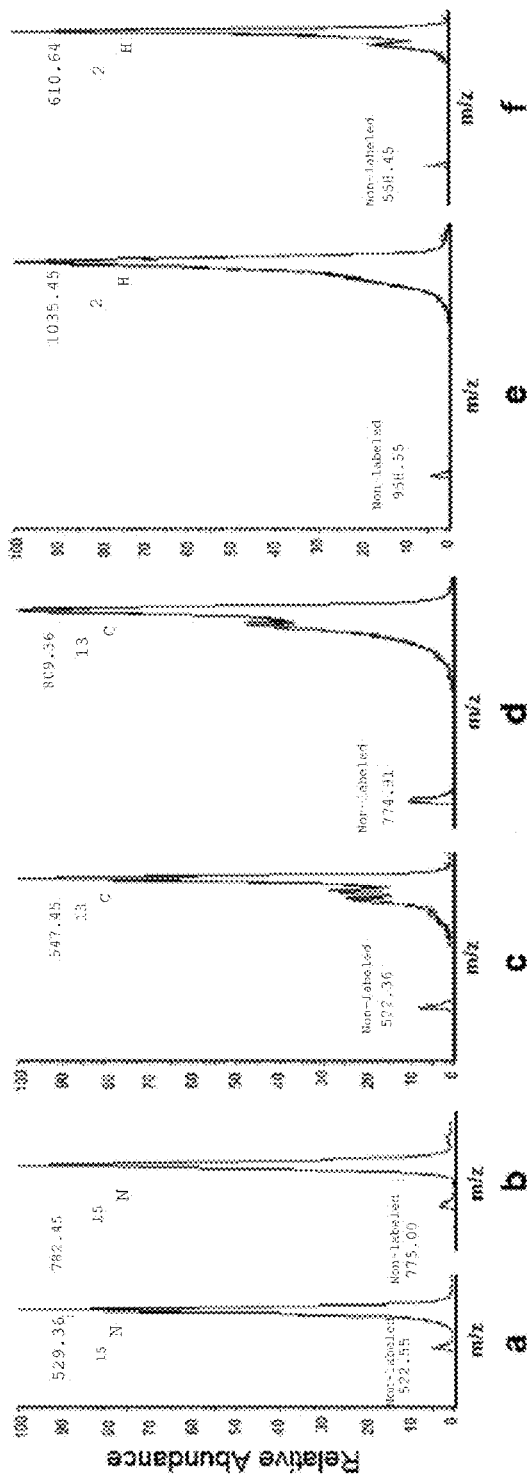
FIGS. 6 a-f provide graphical representations of LC MS results showing isotopic enrichment of EnvZB tryptic fragments. (a) $^{15}N$ enrichment for HLFQPFVR (SEQ ID NO. 6); (b) $^{15}N$ enrichment for EIETALYPGSIEVK (SEQ ID NO. 5); (c) $^{13}C$ enrichment for HLFQPFVR (SEQ ID NO. 8); (d) $^{13}C$ enrichment for EIETALYPGSIEVK (SEQ ID NO. 7); (e) $^{2}H$ enrichment for AWFQVEDDGPGIAPEQR (SEQ ID NO. 9); (f) $^{2}H$ enrichment for AVANMVVNAAR (SEQ ID NO. 10)

The use of media enriched with [$^{15}$N]NH$_4$Cl, [$^{13}$C]glucose, and D$_2$O (2H) showed no significant decrease in the expression level of target proteins with 20 times condensed cultures. LC-MS analyses of the tryptic fragments obtained from EnvZB, E1B19K150, and CaM were conducted. The obtained tryptic fragments are described in Table 1 below. The LC MS results for EnvZB are shown in FIG. 6. The data showed that the levels of incorporation were consistent for all the peptides being studied, with maximum labeling efficiencies higher than 90% (Table 1). The efficiency of isotopic incorporation was analyzed based on retention time and tandem-MS information by integrating the areas of peaks corresponding to the isotope labeled peptides as performed in the art. The ratio of labeled peak area to unlabeled peak area was employed for estimation of the amount of isotopic incorporation. The conventional IPTG-inducible SPP system usually resulted in as high as 20% unlabeled peaks. Using the present Trp- and His-inducible systems, this unlabeled background was significantly reduced, resulting in a maximum yield of 99% labeled peaks (Table 1).

TABLE 1

Isotopic incorporation rates of several peptides generated from proteins produced by the eSPP dual-induction, system

| Peptide Type[a] | Isotope | Peptide sequence | SEQ. ID. NO. | Labeled yield (%) | Labeled efficiency (%)[b] |
|---|---|---|---|---|---|
| a | $^{15}$N | EIETALYPGSIEVK | 5 | 97 | 94 |
|   |   | HLFQPFVR | 6 | 97 | 94 |
|   | $^{13}$C | EIETALYPGSIEVK | 7 | 97 | 92 |
|   |   | HLFQPEVIZ | 8 |   |   |
|   | $^{2}$H | AWFOVEDDOPDIAPEOR | 9 | 99 | ND |
|   |   | AVANNIVVNAAR | 10 | 99 | ND |
| b | $^{15}$N | FLINGSSOAK | 11 | 98 | 82 |
|   |   | TLDFSITGR | 12 | 99 | 90 |
|   | $^{13}$C | FLWGSSOAK | 13 | 98 | 69 |
|   |   | TLDFSTPGR | 14 | 98 | 89 |
|   | $^{2}$H | FLWGSSOAK | 15 | 96 | 67 |
|   |   | TLDFSTPGR | 16 | 99 | 78 |
| c | $^{15}$N | LLLLSSVRPAIIPTEEQQ | 17 | 97 | 89 |
|   |   | AAAAVAFLSF1K | 18 | 95 | 87 |
|   | $^{13}$C | LLLLSSVRPATIFTEEQQ | 19 | 94 | 86 |
|   |   | AAAAVAFLSF1K | 20 | 95 | 88 |
|   | $^{2}$H | LLLLSSVRFAUPTEEQQ | 21 | 94 | 81 |
|   |   | AAAAVAFISFIK | 22 | 93 | 76 |
| c | $^{15}$N | LTDEEVDEMIR | 23 | 98 | 93 |
|   |   | EAFSLFDKDGDOTITTK | 24 | 97 | 88 |
|   | $^{13}$C | LTDEEVDEMIR | 25 | 97 | 91 |
|   |   | EAFSLFDKDODGTITTK | 26 | 96 | 90 |
|   | $^{2}$H | LTDEEVDEMIR | 27 | 96 | 89 |
|   |   | EAFSLEDKDGDGITITIC | 28 | 93 | 82 |

[a] a and b, peptides from the EIB19K150 protein with the Trp system; c, peptides from CaM with the His system.
[b] ND, not determined.

Example 2

As a further example, the SPP system of the present invention is used for a therapeutic screening system for anti-influenza A virus. This is achieved by targeting the M2 proton channel. A truncated form of M2 protein, M2 (2-49), can be expressed in E. coli only in the presence of the channel inhibitor, Amantadine. Furthermore, M2(2-49) retains channel sensitivity to Amantadine even with the N-terminal fusion of GFP or Protein S tag (PST). Out of fifteen drugs tested, eight were found to allow cells to produce GFP-M2 (2-49). These eight drugs showed surprisingly a high correlation between cell culture density and their effectiveness of channel inhibition. Notably, for the GFP-M2 (2-49) production, the Single-Protein Production (SPP) system is supposed to block cell growth completely. However, GFP-M2(2-49) expression in the presence of channel inhibitors was found to override the cell growth inhibition caused by the SPP system. Hence, simple measurement of E. coli cell growth occurring only in the presence of effective M2 inhibitors may be used for the high throughput drug screening for M2 channel instead of its tedious biological analysis. Two potential inhibitors for M2 (V27A) mutants were identified using this method, which inhibit this mutant channel as well as the wild-type M2 channel.

What is claimed:

1. A system for expressing a single target protein in an *E. coli* cell comprising:
    (i) an isolated *E. coli* tryptophan auxotroph; and
    (ii) an expression vector comprising an isolated nucleic acid sequence encoding *E. coli* MazF protein with W14F and W83L substitutions, a sequence-specific mRNA endoribonuclease.

2. The system of claim 1, further comprising an expression vector comprising an isolated nucleic acid sequence encoding a target protein.

3. The system of claim 1, further comprising a composition suitable to induce the sequence-specific mRNA endoribonuclease.

4. The system of claim 2 further comprising a composition comprising tryptophan.

5. A system for expressing a single target protein in an *E. coli* cell comprising:
    (i) an isolated *E. coli* histidine auxotroph; and
    (ii) an expression vector comprising an isolated nucleic acid sequence encoding *E. coli* MazF protein with G27K and H28R substitutions, a sequence-specific mRNA endoribonuclease.

6. The system of claim 5, further comprising an expression vector comprising an isolated nucleic acid sequence encoding a target protein.

7. The system of claim 5, further comprising a composition suitable to induce the sequence-specific mRNA endoribonuclease.

8. The system of claim 7, further comprising a composition comprising histidine.

* * * * *